United States Patent [19]

Hosoda

[11] Patent Number: 4,636,561

[45] Date of Patent: Jan. 13, 1987

[54] SPIROINDOLINENAPHTHOXADINE PHOTOCHROMIC COMPOUNDS

[75] Inventor: Masahiro Hosoda, Kyoto, Japan

[73] Assignee: Unitika Ltd., Kyoto, Japan

[21] Appl. No.: 804,951

[22] Filed: Dec. 5, 1985

[30] Foreign Application Priority Data

Dec. 11, 1984 [JP] Japan .............................. 59-261306
Mar. 7, 1985 [JP] Japan .................................. 60-45387

[51] Int. Cl.$^4$ ........................................... C07D 498/10
[52] U.S. Cl. ....................................... 544/71; 350/354
[58] Field of Search ........................................... 544/71

[56] References Cited

U.S. PATENT DOCUMENTS

| | | | |
|---|---|---|---|
| 3,562,172 | 2/1971 | Ono et al. | 544/71 X |
| 3,578,602 | 5/1971 | Ono et al. | 544/71 X |
| 4,215,010 | 7/1980 | Hovey et al. | 544/71 X |
| 4,342,668 | 8/1982 | Hovey et al. | 544/71 X |

FOREIGN PATENT DOCUMENTS

WO85/02619 6/1985 PCT Int'l Appl. .

OTHER PUBLICATIONS

Yoshihara et al, Chemical Abstracts, vol. 79, (1973), 20306p.

Primary Examiner—Richard L. Raymond
Attorney, Agent, or Firm—Sughrue, Mion, Zinn, Macpeak, and Seas

[57] ABSTRACT

A photochromic compound represented by formula (I):

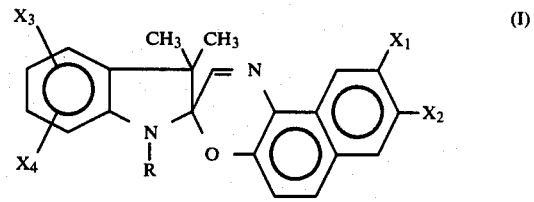

wherein one of $X_1$ and $X_2$ represents a hydroxyl group, a sulfonic acid group or an alkali metal sulfonate base, and the other of $X_1$ and $X_2$ represents a hydrogen atom; $X_3$ and $X_4$ each represents a hydrogen atom, a lower alkyl group having from 1 to 3 carbon atoms, a lower alkoxy group having from 1 to 3 carbon atoms, a halogen atom, a nitro group or a cyano group; and R represents a straight chain alkyl group having from 1 to 30 carbon atoms. The compound exhibits excellent color developability.

5 Claims, No Drawings

SPIROINDOLINENAPHTHOXADINE PHOTOCHROMIC COMPOUNDS

FIELD OF THE INVENTION

This invention relates to a photochromic compound which undergoes a reversible color change upon irradiation with light. The term "photochromic compound" herein means a compound having a tendency to develop a color upon exposure to light of a given wavelength and returns to its original color in the dark, i.e., a compound which undergoes a reversible color change.

BACKGROUND OF THE INVENTION

It is hitherto known that spironaphthoxadine derivatives show photochromism. As a result, these compounds are now being employed in sunglasses, optical filters, curtains, etc. by dissolving or dispersing them in high polymeric binders.

U.S. Pat. No. 3,578,602 discloses 1,3,3-trimethylspiro[indoline-2,3'-(3H)-naphtho(2,1-b)-1,4-oxadine] and proposes a photochromic material prepared by coating a solution of this compound in an appropriate high polymeric binder on a transparent support and drying. However, this material has not yet been put in practical use since the change in the optical density at the maximum absorption wavelength in the state activated by light irradiation (hereinafter referred to as "color developability") is not satisfactory.

In order to overcome the above-described problem, an attempt was made in U.S. Pat. No. 4,215,010 to enhance color developability by introducing a methoxy group, an ethoxy group or a halogen atom into the 8'- or 9'-position of the aforesaid spironaphthoxadine compound, but such a proposal is still unsatisfactory from the standpoint of practical use.

SUMMARY OF THE INVENTION

An object of this invention is to provide a spironaphthoxadine derivative having excellent color developability.

As a result of extensive and intensive investigations, it has now been found that spironaphthoxadine derivatives exhibiting excellent color developability can be obtained by introducing a hydroxyl group, a sulfonic acid group or an alkali metal sulfonate base into the 8'- or 9'-position of 1,3,3-trimethylspiro[indoline-2,3'-(3H)-naphtho(2,1-b)-1,4-oxadine].

That is, the present invention relates to a photochromic compound represented by formula (I):

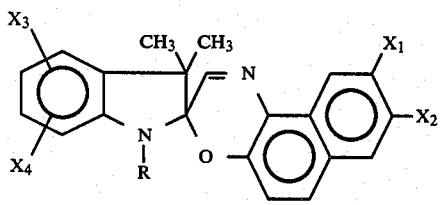

wherein one of $X_1$ and $X_2$ represents a hydroxyl group, a sulfonic acid group or an alkali metal sulfonate base, and the other of $X_1$ and $X_2$ represents a hydrogen atom; $X_3$ and $X_4$ each represents a hydrogen atom, a lower alkyl group having from 1 to 3 carbon atoms, a lower alkoxy group having from 1 to 3 carbon atoms, a halogen atom, a nitro group or a cyano group; and R represents a straight chain alkyl group having from 1 to 30 carbon atoms.

DETAILED DESCRIPTION OF THE INVENTION

In the above-described formula (I), preferred examples of the sulfonic acid group or alkali metal sulfonate base for $X_1$ or $X_2$ include $-SO_3H$, $-SO_3Na$ and $-SO_3K$. For $X_3$ and $X_4$, the lower alkyl group includes a methyl group, an ethyl group and a propyl group; the lower alkoxy group includes a methoxy group, an ethoxy group and a propoxy group; and the halogen atom includes a fluorine atom, a chlorine atom, a bromine atom and an iodine atom.

The preferred photochromic compound of the present invention is a compound represented by formula (I) wherein one of $X_1$ and $X_2$ represents a hydroxyl group or a sodium sulfonate group ($-SO_3Na$), and the other of $X_1$ and $X_2$ represents a hydrogen atom; $X_3$ and $X_4$ each represents a lower alkyl group such as a methyl group, a lower alkoxy group such as a methoxy group or a halogen atom such as a chlorine atom and a bromine atom; and R represents a methyl group, an isopropyl, a hexadecyl group or an octadecyl group.

The compounds represented by the formula (I) can be synthesized by reacting 1-nitroso-2,7-dihydroxynaphthalene, 1-nitroso-2,6-dihydroxynaphthalene, 1-nitroso-2-naphthol-6-sulfonic acid, 1-nitroso-2-naphthol-7-sulfonic acid, sodium or potassium 1-nitroso-2-naphthol-6-sulfonate or sodium or potassium 1-nitroso-2-naphthol-7-sulfonate with an indole iodide derivative in the presence of triethylamine.

Specific examples of the indole iodide derivative which can be used in the above reaction are 1,2,3,3-tetramethylindole iodide, 5-chloro-1,2,3,3-tetramethylindole iodide, 5-methoxy-1,2,3,3-tetramethylindole iodide 1,2,3,3,4,5-hexamethylindole iodide, 1-pentyl-2,3,3-trimethylindole iodide, 1-hexadecyl-2,3,3-trimethylindole iodide and 1-octadecyl-2,3,3-trimethylindole iodide. These indole iodide derivatives can be prepared in accordance with a known Menschutkin reaction as described, for example, in Org. Syn., Coll. Vol. 4, 641 (1963).

When the photochromic compound according to the present invention is irradiated with ultraviolet rays in the form of its solution or as a dispersion in water, an appropriate organic solvent or an appropriate high polymeric binder, it immediately develops a blue color having a maximum absorption wavelength in the vicinity of 620 nm, and when the thus colored compound is allowed to stand in the dark or irradiated with visible rays, it returns to its original colorless state. Such a color change is reversibly repeated and, accordingly, the compound of the present invention possesses a satisfactory photochromic property.

The organic solvents which can be used for dissolving or dispersing the photochromic compounds of this invention can be selected from a wide variety including, for example, methyl alcohol, ethyl alcohol, acetone, methyl ethyl ketone, chloroform, methylene chloride, ethyl acetate, tetrahydrofuran, dioxane, methyl cellosolve, dimethyl sulfoxide, etc.

Examples of the high polymeric binders for dissolving or dispersing the compounds of this invention are acrylate type polymers, e.g., polymethyl methacrylate; styrene type polymers, e.g., polystyrene; polyester type polymers, e.g., polycarbonate; polyether type polymers, e.g., polyethylene oxide; polyamide type polymers, e.g., nylon 6; polyolefin type polymers, e.g., polyethylene; cellulose type polymers, e.g., ethyl cellulose; polyvinyl alcohol, polyvinyl butyral, polyvinyl acetate, polyvinyl chloride, polyvinylidene chloride, polyglycidyl methacrylate, poly-N-vinylcarbazole; and copolymers comprising the monomer units constituting these homopolymers; and mixtures thereof.

Of the compounds (I) according to the present invention, those wherein one of $X_1$ and $X_2$ represents a sulfonic acid group or an alkali metal salt thereof are water-soluble or at least partially water-soluble and, therefore, can be incorporated in synthetic fibers or resin molded articles made of polyvinyl alcohol, nylon 6, polyurethane, polymethyl methacrylate, polyethylene terephthalate, polyglycidyl acrylate, acetate, etc. in accordance with a known dyeing method for direct dyes or acid dyes. The amount of the compound of this invention to be contained in these high polymers preferably ranges from 0.1 to 50%, more preferably 5 to 20%, by weight based on the high polymers.

Further, the photochromic compounds of this invention can be applied to light-controlling materials, such as light-controlling plastic lenses, window shades and the like, display devices, electronic devices, actinometers, decorative articles and the like.

The present invention will now be illustrated in greater detail with reference to the following examples, but it should be understood that these examples are in no way intended to limit the present invention.

EXAMPLE 1

Twenty grams of 1-nitroso-2,7-dihydroxynaphthalene were dissolved in 200 ml of ethanol, and the solution was heated to about 80° C. To the solution was added dropwise 100 ml of an ethanol solution containing 13 g of triethylamine and 35 g of 1,2,3,3-tetramethylindole iodide over a period of 30 minutes, and the mixture was refluxed for 2 hours. The reaction mixture was distilled under reduced pressure until the excess ethanol was reduced to about one-fourth. Upon cooling, there were precipitated crude crystals of 1,3,3-trimethyl-9'-hydroxy-spiroindolinenaphthoxadine. Recrystallization from ethyl alcohol gave 15 g of crystals havng a melting point of 167° to 173° C.

Elemental Analysis:

|  | C | H | N |
| --- | --- | --- | --- |
| Calcd. (%): | 76.7 | 5.9 | 8.1 |
| Found (%): | 76.5 | 6.0 | 8.0 |

In 150 ml of toluene were dissolved 0.1 g of the above prepared compound and 10 g of polymethyl methacrylate, and the solution was casted over a glass plate to a film thickness of 100 μm and dried. The film was irradiated with light using a high pressure mercury lamp (500 W; manufactured by Ushio Electric Inc.) through a cut filter "UV-31" (a trade name, manufactured by Toshiba Glass Co., Ltd.). The film which was colorless and transparent before light irradiation turned deep blue after light irradiation for 30 seconds.

When the thus colored film was allowed to stand in the dark for about 10 seconds, the film returned to colorless state. The maximum absorption wavelength ($\lambda_{max}$) in the activated state under light irradiation was 620 nm. The change of absorbance (ΔOD) at the $\lambda_{max}$ is shown in the Table below.

EXAMPLE 2

In the same manner as in Example 1 but using 5-chloro-1,2,3,3-tetramethylindole iodide in place of 1,2,3,3-tetramethylindole iodide, 5-chloro-1,3,3-trimethyl-9'-hydroxy-spiroindolinenapthoxadine having a melting point of 203° to 206° C. was synthesized.

Elemental Analysis:

|  | C | H | N |
| --- | --- | --- | --- |
| Calcd. (%): | 69.7 | 5.0 | 7.4 |
| Found (%): | 70.2 | 5.4 | 7.2 |

When a film was produced from the above prepared compound and irradiated with light for 30 seconds in the same manner as in Example 1, a deep blue color developed. The $\lambda_{max}$ was 618 nm. The change of absorbance (ΔOD) at the $\lambda_{max}$ is shown in the Table below.

EXAMPLE 3

In the same manner as in Example 1 but using 1-nitroso-2,6-dihydroxynaphthalene in place of 1-nitroso-2,7-dihydroxynaphthalene, 1,3,3-trimethyl-8'-hydroxy-spiroindolinenaphthoxadine having a melting point of 173° to 177° C. was synthesized.

Elemental Analysis:

|  | C | H | N |
| --- | --- | --- | --- |
| Calcd. (%): | 76.7 | 5.9 | 8.1 |
| Found (%): | 76.8 | 6.1 | 8.2 |

When a film was produced from the above prepared compound and irradiated with light for 30 seconds in the same manner as in Example 1, a deep blue color developed. The $\lambda_{max}$ was 622 nm. The change of absorbance at the $\lambda_{max}$ is shown in the Table below.

EXAMPLE 4

In the same manner as in Example 1 but using 1-nitroso-2,6-dihydroxynaphthalene and 5-methoxy-1,2,3,3-tetramethylindole iodide as starting compounds, 5-methoxy-1,3,3-trimethyl-8'-hydroxy-spiroindolinenaphthoxadine having a melting point of 193° to 196° C. was obtained.

When a film was produced from the above prepared compound and irradiated with light for 30 seconds in the same manner as in Example 1, a deep blue color developed. The $\lambda_{max}$ was 621 nm. The change in absorbance at the $\lambda_{max}$ is shown in the Table below.

EXAMPLE 5

In the same manner as in Example 3 but using 1,2,3,3,4,5-hexamethylindole iodide in place of 1,2,3,3-tetramethylindole iodide, 1,3,3,4,5-pentamethyl-8'-hydroxyspiroindolinenaphthoxadine having a melting point of 223° to 225° C. was synthesized.

When a film was produced from the above prepared compound and irradiated with light for 30 seconds in the same manner as in Example 1, a deep blue color developed. The $\lambda_{max}$ was 628 nm. The change in absorbance at the $\lambda_{max}$ is shown in the Table below.

EXAMPLES 6 TO 8

In the same manner as in Example 1 but replacing 1,2,3,3-tetramethylindole iodide with 1-isopropyl-2,3,3-trimethylindole iodide (Example 6), 1-hexadecyl-2,3,3- trimethylindole iodide (Example 7) or 1-octadecyl-2,3,3-trimethylindole iodide (Example 8), the respective compound of the formula (I) wherein $X_1$, $X_2$, $X_3$, $X_4$ and R are as shown in the Table below was synthesized.

When a film produced from each of the resulting compounds was irradiated with light in the same manner as in Example 1, a deep blue color developed in each case. The $\lambda_{max}$ was 618 nm, 617 nm or 617 nm, respectively.

EXAMPLE 9

In 250 ml of methyl alcohol was dissolved 24.6 g of sodium 1-nitroso-2-naphthol-6-sulfonate, and the solution was heated to 65° C. To the resulting solution was added dropwise 100 ml of a methyl alcohol solution containing 10.2 g of triethylamine and 27 g of 1,2,3,3-tetramethylindole iodide over a period of 30 minutes, followed by refluxing for 2 hours The mixture was distilled under reduced pressure until the excess methyl alcohol was reduced to about one-fourth. The residue was cooled to precipitate crude crystals of sodium 1,3,3-trimethyl-8'-sulfonate-spiroindolinenaphthoxadine. Recrystallization from methyl alcohol yielded 12 g of crystals having a melting point of 295° to 298° C.

Elemental Analysis:

|  | C | H | N | O | S |
|---|---|---|---|---|---|
| Calcd. (%): | 61.4 | 4.4 | 6.5 | 14.9 | 7.4 |
| Found (%): | 61.2 | 4.3 | 6.2 | 14.3 | 7.0 |

The infrared absorption spectra showed stretching vibration of an S=O bond at 665 cm$^{-1}$ due to the SO$_3$Na group.

In 150 ml of acetone were dissolved 0.1 g of the above prepared compound and 10 g of polymethyl methacrylate, and the resulting solution was casted over a horizontally placed glass plate to a thickness of 100 μm and dried. The film was irradiated with light in the same manner as in Example 1. Upon light-irradiation for 30 seconds, the film which was colorless and transparent before light-irradiation turned to deep blue. When the thus colored film was allowed to stand in the dark for about 20 seconds, it returned to its original colorless state. The maximum absorption wavelength ($\lambda_{max}$) in the activated state under light-irradiation ws 608 nm. The change of absorbance (ΔOD) at the $\lambda_{max}$ is shown in the Table below.

Further, a solution comprising 1.0 g of the above-described sodium 1,3,3-trimethyl-8'-sulfonate-spiroindolinenaphthoxadine, 10.0 g of a nonionic surface active agent ("Noigen EA-120", a trade name manufactured by Dai-Ichi Kogyo Seiyaku Co., Ltd.) and 1,000 ml of water was heated to 90° C. A polymethyl methacrylate plate of 3 mm in thickness was immersed in the resulting hot dye bath for 30 minutes. The plate after the immersion treatment was colorless and transparent, but, upon irradiation with light for 30 seconds, a deep blue color developed. When the thus colored plate was allowed to stand in the dark, it returned to its original colorless state in about 2 minutes.

EXAMPLE 10

In the same manner as in Example 9 but using sodium 1-nitroso-2-naphthol-7-sulfonate in place of sodium 1-nitroso-2-naphthol-6-sulfonate, sodium 1,3,3-trimethyl-9'-sulfonate-spiroindolinenaphthoxadine having a melting point of 291° to 294° C. was synthesized.

Elemental Analysis:

|  | C | H | N | O | S |
|---|---|---|---|---|---|
| Calcd. (%): | 61.4 | 4.4 | 6.5 | 14.9 | 7.4 |
| Found (%): | 61.0 | 4.9 | 6.3 | 14.2 | 7.1 |

When a film was produced from the above prepared compound and irradiated with light for 30 seconds in the same manner as in Example 1, a deep blue color developed. The $\lambda_{max}$ was 610 nm. The change in absorbance at the $\lambda_{max}$ is shown in the Table below.

Further, a polymethyl methacrylate plate was treated with the above compound by the same dyeing method as in Example 9 and irradiated with light in the same manner as in Example 1. The plastic plate which was colorless and transparent before light-irradiation turned to deep blue upon light-irradiation. When the thus colored plastic plate was allowed to stand in the dark, it returned to its original colorless state in about 2 minutes.

EXAMPLE 11

In the same manner as in Example 9 but using sodium 1-nitroso-2-naphthol-6-sulfonate and 5-methoxy-1,2,3,3-tetramethylindole iodide as starting compounds, sodium 5-methoxy-1,3,3-trimethyl-8 α-sulfonate-spiroindolinenaphthoxadine having a melting point of 322° to 324° C. was synthesized.

When a film was produced from the above prepared compound in the same manner as in Example 9 and irradiated with light for 30 seconds in the same manner as in Example 10, a deep blue color developed. The $\lambda_{max}$ was 613 nm. The change in absorbance at the $\lambda_{max}$ is shown in the Table below.

Further, a polymethyl methacrylate plate was treated with the above compound by the same dyeing method as in Example 9 and irradiated with light in the same manner as in Example 1. The plastic plate which was colorless and transparent before light-irradiation turned to deep blue upon irradiation with light. When the thus colored plastic plate was allowed to stand in the dark, it returned to its original colorless state in about 2 minutes.

EXAMPLE 12

In the same manner as in Example 9 but using potassium 1-nitroso-2-naphthol-6-sulfonate and 5-chloro-1,2,3,3-tetramethylindole iodide as starting compounds, potassium 5-chloro-1,3,3-trimethyl-8'-sulfonate-spiroindolinenaphthoxadine having a melting point of 332° to 335° C. was synthesized.

When a film was produced from the above prepared compound in the same manner as in Example 9 and irradiated with light for 30 seconds in the same manner as in Example 1, a deep blue color developed. The $\lambda_{max}$ was 611 nm. The change in absorbance at the $\lambda_{max}$ is shown in the Table below.

Further, a polymethyl methacrylate plate was treated with the above compound in accordance with the same dyeing method as in Example 9, and the plate was irradiated with light in the same manner as in Example 1. The plastic plate which was colorless and transparent before light-irradiation developed a deep blue color upon light-irradiation. When the thus colored plate was allowed to stand in the dark, it returned to a colorless state in about 2 minutes.

EXAMPLE 13

In the same manner as in Example 9 but using sodium 1-nitroso-2-naphthol-6-sulfonate and 1-octadecyl-2,3,3-trimethylindole iodide as starting compounds, sodium 1-octadecyl-3,3-dimethyl-8'-sulfonate-spiroindolinenaphthoxadine having a melting point of 347° to 349° C. was synthesized.

A film was produced from the above prepared compound in the same manner as in Example 9. When the film was irradiated with light for 30 seconds in the same manner as in Example 1, a deep blue color developed. The $\lambda_{max}$ was 616 nm. The change in absorbance at the $\lambda_{max}$ is shown in the Table below.

COMPARATIVE EXAMPLES 1 AND 2

In order to demonstrate the excellent color developability of the compounds of this invention over the conventional spironaphthoxadine derivatives, comparative tests were conducted as follows.

1,3,3-Trimethyl-spiroindolinenaphthoxadine (Comparative Example 1) or 1,3,3-trimethyl-9'-methoxy-spiroindolinenaphthoxadine (Comparative Example 2) which was prepared by the methods disclosed in U.S. Pat. Nos. 3,578,602 and 4,215,010 was dissolved in polymethyl methacrylate to a concentration of 1.0% by weight, and a film having a thickness of 100 μm was produced from each solution. The film was irradiated with light in the same manner as described in Example 1, and the change in absorbance at the $\lambda_{max}$ in the activated state was determined. The results obtained are shown in the Table below.

It can be seen from the Table below that the films prepared from these conventional compounds undergo a smaller change of absorbance as compared with the compounds of the present invention.

TABLE

| Example No. | $X_1$ | $X_2$ | $X_3$ and $X_4$ | | R | $\Delta$OD at $\lambda_{max}$* |
|---|---|---|---|---|---|---|
| Example 1 | OH | H | H | | CH$_3$ | 0.90 |
| Example 2 | OH | H | 5-Cl | H | CH$_3$ | 0.79 |
| Example 3 | H | OH | H | | CH$_3$ | 0.75 |
| Example 4 | H | OH | 5-CH$_3$O | H | CH$_3$ | 0.82 |
| Example 5 | H | OH | 4-CH$_3$ | 5-CH$_3$ | CH$_3$ | 0.88 |
| Example 6 | OH | H | H | | isoC$_3$H$_7$ | 0.72 |
| Example 7 | OH | H | H | | C$_{16}$H$_{33}$ | 0.71 |
| Example 8 | OH | H | H | | C$_{18}$H$_{37}$ | 0.67 |
| Example 9 | H | SO$_3$Na | H | | CH$_3$ | 0.78 |
| Example 10 | SO$_3$Na | H | H | | CH$_3$ | 0.73 |
| Example 11 | H | SO$_3$Na | 5-CH$_3$O | H | CH$_3$ | 0.81 |
| Example 12 | H | SO$_3$K | 5-Cl | H | CH$_3$ | 0.69 |
| Example 13 | H | SO$_3$Na | H | | C$_{18}$H$_{37}$ | 0.62 |
| Comparative Example 1 | H | H | H | | CH$_3$ | 0.43 |
| Comparative Example 2 | OCH$_3$ | H | H | | CH$_3$ | 0.62 |

Note:
*determined at 28 ± 0.5° C.

While the invention has been described in detail and with reference to specific embodiments thereof, it will be apparent to one skilled in the art that various changes and modifications can be made therein without departing from the spirit and scope thereof.

What is claimed is:

1. A photochromic compound represented by formula (I):

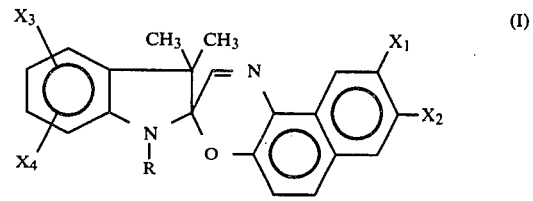

wherein one of $X_1$ and $X_2$ represents a hydroxyl group, and the other of $X_1$ and $X_2$ represents a hydrogen atom; $X_3$ and $X_4$ each represents a hydrogen atom, a lower alkyl group having from 1 to 3 carbon atoms, a lower alkoxy group having from 1 to 3 carbon atoms, a halogen atom, a nitro group or a cyano group; and R represents a straight chain alkyl group having from 1 to 30 carbon atoms.

2. A photochromic compound as in claim 1, wherein R is a methyl group.

3. A photochromic compound as in claim 1, wherein $X_1$ is a hydroxyl group.

4. A photochromic compound as in claim 1, wherein $X_2$ is a hydroxyl group.

5. A photochromic compound as in claim 1, wherein R is selected from the group consisting of a methyl group, an isopropyl, a hexadecyl group and an octadecyl group.

* * * * *